United States Patent
Palmer et al.

(10) Patent No.: US 9,773,399 B2
(45) Date of Patent: Sep. 26, 2017

(54) DIAGNOSTIC TEST DEVICE WITH AUDIBLE FEEDBACK

(71) Applicant: Church & Dwight Co., Inc., Princeton, NJ (US)

(72) Inventors: Mathew Palmer, Cottenham (GB); Giles H. W. Sanders, Fowlmere (GB); Nicholas J. Wooder, Chrishall Royston (GB); Albert R. Nazareth, Mercerville, NJ (US); Timothy Snowden, Howell, NJ (US); Ovidiu Romanoschi, Highland Park, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 14/776,579

(22) PCT Filed: Mar. 5, 2014

(86) PCT No.: PCT/US2014/020536
§ 371 (c)(1),
(2) Date: Sep. 14, 2015

(87) PCT Pub. No.: WO2014/158850
PCT Pub. Date: Oct. 2, 2014

(65) Prior Publication Data
US 2016/0027283 A1    Jan. 28, 2016

Related U.S. Application Data

(60) Provisional application No. 61/779,615, filed on Mar. 13, 2013.

(51) Int. Cl.
*G08B 23/00* (2006.01)
*G08B 21/18* (2006.01)
(Continued)

(52) U.S. Cl.
CPC .............. *G08B 21/18* (2013.01); *A61B 5/145* (2013.01); *A61B 5/741* (2013.01); *A61B 5/7415* (2013.01);
(Continued)

(58) Field of Classification Search
CPC ............................. G01N 1/00; G01N 2201/00
See application file for complete search history.

(56) References Cited

U.S. PATENT DOCUMENTS

| | | |
|---|---|---|
| 5,739,041 A | 4/1998 | Nazareth et al. |
| 5,846,835 A | 12/1998 | Sisbarro et al. |

(Continued)

FOREIGN PATENT DOCUMENTS

| | | |
|---|---|---|
| EP | 2 228 005 | 9/2010 |
| WO | 2005088599 A1 | 9/2005 |

(Continued)

*Primary Examiner* — Shirley Lu
(74) *Attorney, Agent, or Firm* — Church & Dwight Co., Inc.

(57) ABSTRACT

Diagnostic test devices improve communication to a user thereof through provision of audible output. The test device can include a test member, such as lateral flow assay test strip. The test device further includes an electronic communication circuit that can comprise an audio output element as well as a microcontroller. Other elements in the electronic communication circuit includes one or more sensor elements, a display element, and one or more switching elements.—Methods provide indicia for operation of a test device that comprise steps for assembly of a diagnostic test device that provides for audio output.

19 Claims, 7 Drawing Sheets

(51) Int. Cl.
    *G01N 33/74*     (2006.01)
    *A61B 5/00*     (2006.01)
    *A61B 5/145*     (2006.01)
    *G01N 33/543*     (2006.01)
    *G08B 3/00*     (2006.01)

(52) U.S. Cl.
    CPC ....... *G01N 33/54386* (2013.01); *G01N 33/74* (2013.01); *G08B 3/00* (2013.01)

(56) References Cited

U.S. PATENT DOCUMENTS

| | | | |
|---|---|---|---|
| 6,046,057 A | 4/2000 | Nazareth et al. | |
| 6,099,476 A | 8/2000 | Engel et al. | |
| 6,277,650 B1 | 8/2001 | Nazareth et al. | |
| 6,319,676 B1 | 11/2001 | Nazareth et al. | |
| 6,485,982 B1 | 11/2002 | Charlton et al. | |
| 6,665,966 B1 | 12/2003 | Beck | |
| 6,767,714 B2 | 7/2004 | Nazareth et al. | |
| 7,045,342 B2 | 5/2006 | Nazareth et al. | |
| 7,214,542 B2 | 5/2007 | Hutchinson | |
| 7,220,597 B2 | 5/2007 | Zin et al. | |
| 7,499,170 B2 | 3/2009 | Sasaki et al. | |
| 7,763,454 B2 | 7/2010 | Nazareth et al. | |
| 7,776,618 B2 | 8/2010 | Nazareth et al. | |
| 8,211,711 B2 | 7/2012 | Nazareth et al. | |
| 2002/0042082 A1 | 4/2002 | Nazareth et al. | |
| 2003/0211625 A1 | 11/2003 | Cohan et al. | |
| 2004/0171174 A1 | 9/2004 | Nazareth et al. | |
| 2005/0036077 A1 | 2/2005 | Khan et al. | |
| 2005/0124375 A1 | 6/2005 | Nowosielski et al. | |
| 2006/0008896 A1 | 1/2006 | Nazareth et al. | |
| 2007/0185679 A1* | 8/2007 | Petruno ............. | G01N 21/8483 702/117 |
| 2007/0204696 A1 | 9/2007 | Braun et al. | |
| 2008/0051640 A1 | 2/2008 | Illif | |
| 2008/0213920 A1 | 9/2008 | Nazareth et al. | |
| 2009/0112617 A1 | 4/2009 | Jung et al. | |
| 2009/0149717 A1 | 6/2009 | Brauer et al. | |
| 2010/0049016 A1 | 2/2010 | Aronowitz et al. | |
| 2010/0239460 A1 | 9/2010 | Nazareth et al. | |
| 2010/0240149 A1 | 9/2010 | Nazareth et al. | |
| 2010/0249965 A1* | 9/2010 | Rao ................ | G06F 19/3406 700/94 |
| 2010/0261293 A1 | 10/2010 | Nazareth et al. | |
| 2010/0267166 A1 | 10/2010 | Nazareth et al. | |
| 2010/0317951 A1 | 12/2010 | Rutkowski et al. | |
| 2011/0043527 A1 | 2/2011 | Ording et al. | |
| 2011/0184264 A1 | 7/2011 | Galasso et al. | |
| 2011/0201122 A1 | 8/2011 | Nazareth et al. | |
| 2012/0046606 A1 | 2/2012 | Arefieg | |
| 2012/0083044 A1 | 4/2012 | Sturman et al. | |
| 2012/0232520 A1 | 9/2012 | Sloan et al. | |
| 2013/0203043 A1 | 8/2013 | Ozcan et al. | |

FOREIGN PATENT DOCUMENTS

| | | |
|---|---|---|
| WO | 2008078128 A1 | 7/2008 |
| WO | 2013009589 A1 | 1/2013 |

* cited by examiner

DIAGNOSTIC TEST DEVICE WITH AUDIBLE FEEDBACK

CROSS-REFERENCE TO RELATED APPLICATION

This application is related to U.S. Provisional Patent Application Ser. No. 61/779,615 filed Mar. 13, 2013 and takes priority therefrom.

FIELD OF THE DISCLOSURE

The present disclosure relates to diagnostic test devices that provide user connectivity. More particularly, the test devices include elements that provide for specific feedback to the user, such as through audible means.

BACKGROUND

Many types of ligand-receptor assays have been used to detect the presence of various substances in body fluids, such as urine, saliva, or blood. Some commercially available assays are designed to make a quantitative determination, but in many circumstances all that is required is a qualitative positive/negative indication. Examples of such qualitative assays include blood typing, pregnancy testing, and many types of urinalysis.

U.S. Pat. No. 6,485,982, which is incorporated herein by reference in its entirety, describes a diagnostic test cell or device formed of an elongate outer casing which houses an interior permeable material (such as glass fiber) capable of transporting an aqueous solution by capillary action, wicking, or simple wetting. The casing defines a sample inlet, and interior regions, which are designated as a test volume and a reservoir volume. The reservoir volume is disposed in a section of the test cell spaced apart from the inlet and is filled with sorbent material. The reservoir acts to receive a fluid sample transported along a flow path defined by the permeable material and extending from the inlet and through the test volume. In the test volume is a test site comprising a first protein having a binding site specific to a first epitope of the ligand immobilized in fluid communication with the flow path (e.g., bound to the permeable material or to latex particles entrapped in or bonded to the permeable material). A window, such as a hole or transparent section of the casing, permits observations of the test site through the casing wall. The method of use of the test cell requires the use of a conjugate comprising a second protein bound to colored particles, such as a metal sol or colloid, preferably gold. The conjugate can take two distinct forms, depending on whether the assay is designed to exploit the "sandwich" or "competitive" technique.

U.S. Pat. No. 7,045,342, which is incorporated herein by reference in its entirety, describes a diagnostic test device including a biphasic chromatographic medium. The biphasic substrate is formed of a release medium joined to a capture medium located downstream of the release medium. The release and capture media preferably comprise two different materials, or phases, having different specific characteristics. The two phases are joined together to form a single fluid path such that a solvent front can travel unimpeded from the proximal (upstream) end of the release medium to the distal (downstream) end of the capture medium.

For tests such as those described above, visually observable indicia can be preferred. Such indicia typically have included the presence of agglutination or a color change at a defined site on the assay. More recent efforts have included providing electronic (i.e., digital) signals as the observable indicia. Nevertheless, user interface with diagnostic test devices remain limited. For example, user interface disconnect can lead to user anxiety, such as in relation to uncertainty over the elapsed time between starting a test and obtaining the test result. In typical pregnancy test devices, for example, the elapsed time is typically less than five minutes. During this time, there also can be anxiety over whether the test is indeed progressing normally. For example, although some test devices include a liquid crystal display (LCD) digital readout that can display a static or blinking clock as indicia of a progressing test, such interface can be sufficiently limited so as to not meet user expectations and overcome anxiety. Another user interface disconnect can relate to user uncertainty over whether a sufficient volume of fluid sample (e.g., urine) has been applied in order for the test to progress normally and provide a valid test result. Because of these and other reasons, it would be beneficial to provide a personal use test device with improved communication between the test device and the user.

SUMMARY OF THE DISCLOSURE

The present disclosure relates to diagnostic test devices that include elements useful for carrying out an assay and for providing information related to the assay in an audible format. As an illustrative example, a pregnancy test device can be provided and can include elements for carrying out a test on a fluid sample applied to a receiving member so as to identify the presence of human chorionic gonadotropin (hCG) in the sample that is indicative of a pregnancy status. Such test device beneficially can include further elements that enable the test device to provide a variety of audible indices relating to the operation and results of the assay. Test devices according to the present disclosure thus can provide for increased communication from the test device to a user thereof and make the test device easier for the user to operate, improve understanding of the results of the included assay, and increase user comfort with the test device and user assurance in the reliability of the test device.

In certain embodiments, a diagnostic test device according to the present disclosure can comprise a test member (for example, a test strip, particularly a strip adapted for carrying out a lateral flow assay) and an electronic communication circuit adapted to provide one or more indicia of operation of the test member to a user. More specifically, the electronic communication circuit can include an audio output component. For example, the audio output component can comprise a transducer (i.e., a loudspeaker or a buzzer). The audio output component also can comprise an audio driver that can be a circuit with a built-in oscillator and that can be useful to drive the audio output from the loudspeaker or buzzer. In further embodiments, the audio output component can include an audio chip. Beneficially, the audio chip can include a memory device that is useful to increase the breadth of sounds that can be output from the audio component. Specifically, the memory device can include one or more programmed digital sequences corresponding to an output sound. In light of the variety of audio output elements that can be utilized in the present test device, a wide variety of sounds can be output from the test device. For example, the output sound can be selected from the group consisting of buzzing, a single tone, a series of tones, a melody, a synthesized word or words, a recorded word or words, and combinations thereof. If desired, the test device further can comprise a switching element adapted to enable or disable the audio output component.

In addition to the foregoing, a test device according to the present disclosure can include further components. Specifically, the electronic communication circuit of the test device further can include a microcontroller that can be adapted to signal the audio output component to provide an audible indicia of operation of the test member. Any aspect of the test device that can be adapted to audible description thereof can be relayed by the audio component of the test device under the direction of the microcontroller. As illustrative examples, the microcontroller can be adapted to signal the audio output component to indicate that a defined volume of a fluid sample has been applied to a sample receiving member of the test device for the assay to be carried out. Likewise, the microcontroller can be adapted to signal the audio output component to provide one or more instructions for carrying out the assay. Further, the microcontroller can be adapted to signal the audio output component to indicate one or more times that the assay is processing an applied liquid sample. The microcontroller also can be adapted to signal the audio output component to indicate that the test device has completed processing an applied fluid sample. Still further, the microcontroller can be adapted to signal the audio output component to indicate a test result arising from the test having processed an applied fluid sample. Further to the foregoing examples, the audio output from the present test device need not be limited to the use and results of the test member of the test device. Any further audio output that may be desirable for delivery to a user of the test device can also be provided, particularly in embodiments that incorporate an audio chip and associated memory. For example, marketing information and the like may be communicated by the test device according to the present disclosure.

The diagnostic test device further can comprise components suitable to carry out a test initiation routine. Specifically, the components can include a signaling mechanism in communication with the microcontroller. For example, a switch or sensor may be included to provide indication that a cap of the test device has been removed or that the device has been removed from packaging material (e.g., a foil pouch) so as to ready the test device for use thereof. A defined power on button or capacitive sensing element also may be included to provide manual control for a user to turn the test device on when ready for use thereof. As such, the test device also can include a power source, such as a battery, or any similar element.

The electronic communication circuit of the test further can comprise one or more components adapted to provide input signals to the microcontroller that relate to the test. For example, the electronic communication circuit can include a light source (such as a light emitting diode) and a light sensor. Such components together can form an opto-detector. As such, the word "light" is intended to encompass the entire spectrum of electromagnetic radiation and is not limited to visible light. Thus, for example, ultraviolet and infrared detectors are encompassed. In further embodiments, the electronic communication circuit can include a moisture sensor for providing input signals to the microcontroller, particularly as indication that sufficient sample has been applied to the test device for the assay to proceed normally. Such various elements of the communication circuit thus are desirably positioned within the test device (i.e., within the casing) so that the elements are positioned appropriately for detecting information to be input to the microcontroller.

The diagnostic test device of the present disclosure also can include means for relaying information to a user in a manner other than audibly. For example, the electronic communication circuit can include a display. Specifically, a liquid crystal display (LCD) can be provided so as to allow for digital display of words, images, and the like. Alternatively, the display can be an analog display. Still further, the display can be simply a window in the casing of the test device that enables viewing of a defined section of the assay test strip. Additionally, the test device can include components adapted to cause vibration, and a vibration signal or vibration pattern can be utilized to indicate to a user a defined status of the test device.

As noted above, the test device of the present disclosure includes elements useful for carrying out an assay. Specifically, the test device can include a lateral flow assay that is adapted to detect the presence of an analyte in a sample applied to the assay. In addition to hCG, as noted previously, the analyte can be, for example, luteinizing hormone (LH), follicle stimulating hormone (FSH), estrogen, progesterone, testosterone, or metabolites thereof, or the like. Other analytes—e.g., proteins—can also be detected by the presently disclosed test device.

The present disclosure also encompasses methods for providing one or more indicia of operation of a test to a user. In certain embodiments, the method can comprise combining, in a single casing: the test member; and an electronic communication circuit. The electronic communication circuit can include any combination of the elements otherwise disclosed herein. In certain embodiments, the communication circuit can include: a microcontroller; one or more components adapted to provide input signals to the microcontroller relating to the lateral flow assay; and an audio output component. The method further can comprise programming the microcontroller to respond to a defined input signal by signaling the audio output component to emit a corresponding audio signal. Any audio signal as otherwise disclosed herein can be encompassed by the method.

BRIEF DESCRIPTION OF THE DRAWINGS

The present disclosure is particularly described in reference to the following figures; however, such figures are provided to illustrate only preferred embodiments of the disclosure, and the disclosure is not intended to be limited thereto.

DETAILED DESCRIPTION OF THE DISCLOSURE

The present disclosure now will be described more fully hereinafter with reference to specific embodiments and particularly to the various drawings provided herewith. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a," "an," "the," include plural referents unless the context clearly dictates otherwise.

In one aspect, the present disclosure relates to a test device, such as an over-the-counter (OTC) or point of care (POC) test device, for detecting an analyte in a sample. The device generally includes components suitable for carrying out an assay, such as a lateral flow assay, and also includes components suitable for communicating information relating to the assay to an individual.

The test components in a broad sense can comprise a proximal portion (e.g., a sample receiving member) in fluid communication with a distal portion (e.g., a reservoir). The proximal and distal portions may be interconnected by a substrate material, which itself may form all or part of the proximal and/or distal portion of the device. A sample (e.g., urine) can be directly or indirectly applied to the proximal portion of the device for transport to the distal portion. Preferably, the sample flows across the substrate so as to contact one or more antibodies attached to or otherwise deposited on the substrate. The antibodies can be designed and/or chosen to recognize a variety of analytes. In specific embodiments, a test device according to the present disclosure can be useful for detection of human chorionic gonadotropin (hCG), luteinizing hormone (LH), follicle stimulating hormone (FSH), thyroid stimulating hormone, estrogen, progesterone, testosterone, a metabolite thereof, and combinations thereof. Even further analytes also can be encompassed by the present disclosure.

The devices disclosed herein can make use of a variety of techniques for detecting the presence of an analyte. One example is a sandwich technique wherein one or more antibodies used in the detection comprise a binding member or site which binds to an epitope on the analyte for detection. A labeled antibody binds to the analyte to form a complex in the sample. The analyte, which is bound to the labeled antibody or antibodies, binds with one or more capture antibodies to form a "sandwich," comprising the capture antibody, analyte (or antigen), and the labeled antibody. Each sandwich complex thus produced comprises three components: one capture antibody, one antigen, and one labeled antibody. An antibody used herein can be a polypeptide substantially encoded by an immunoglobulin gene or immunoglobulin genes, or fragments thereof, which may specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The term antibody also can include antibody fragments either produced by the modification of whole antibodies or those synthesized de novo using recombinant DNA methodologies, and further can include "humanized" antibodies made by conventional techniques. Although polyclonal antibodies can be used, antibodies are preferably monoclonal antibodies. A capture antibody according to the disclosure can be an antibody attached to a substrate directly or indirectly, such as a solid substrate. The capture antibody can include at least one binding member that specifically or preferentially binds a particular distinct epitope of an antigen.

In the sandwich technique, the makeup of each sandwich complex can vary depending upon the particular labeled antibody (and thus the particular antigen) included therein. In the same test, there can be multiple different types of sandwiches produced. The sandwich complexes are progressively produced as the test sample with the analyte therein continuously moves along the substrate of the device. As more and more of the analyte/labeled antibody complex is immobilized in sandwich form with the capture antibody or antibodies at the capture site, the label components aggregate and become detectable in that the accumulation of the sandwich complexes at the capture site can be detected in various ways, such as by visual inspection of, for example, color development at the capture site or by a digital readout resulting from the electronic analysis of the aggregate at the capture site as further described herein. Although the sandwich technique is provided as an exemplary embodiment, the devices described herein in relation to the improved communication aspects are not limited to such underlying technique. Rather, other techniques for identifying an analyte in a test sample and forming a detectable signal based on the presence or absence of the analyte in the sample can be utilized.

Exemplary means for forming a detectable signal can comprise the use of a conjugate comprising one or more antibodies bound to detectable label components (e.g., colored particles, such as a metal sol or colloid particles). One or more of the antibodies used in the disclosed devices (e.g., one or two) can be labeled. Any detectable label recognized in the art as being useful in various assays can be used. In particular, the detectable label component can include compositions detectable by reflective, spectroscopic, photochemical, biochemical, immunochemical, or chemical means. As such, the label component produces a detectable signal. For instance, suitable labels include soluble dyes, fluorescent dyes, chemiluminescent compounds, radioisotopes, electron-dense reagents, enzymes, colored particles, or dioxigenin. The label component can generate a measurable signal, such as radioactivity, fluorescent light, color, or enzyme activity, which can be used to identify and quantify the amount of label bound to a capture site. Thus, the label component can also represent the presence or absence of a particular antigen bound thereto, as well as a relative amount of the antigen (e.g., relative to a known standard, threshold standard, or a different standard). The labeled materials can be detected through use of suitable electronic components, including hardware and software, and thus can be communicated to a user via digital signal or similar means. Further detail regarding the production of digital signals in personal use assays is provided, for example, in U.S. Pat. No. 7,214,542 to Hutchinson; U.S. Pat. No. 7,220,597 to Zin et al.; and U.S. Pat. No. 7,499,170 to Sasaki et al., which are incorporated herein by reference.

Devices according to the present disclosure can include one or more standards or internal controls that allow for determination of whether signal development is a true indication of the presence or absence of analyte in the sample or is simply an artifact, such as caused by nonspecific sorption. For example, a negative control site can be prepared identically to the test site, except that immobilization of the capture antibody is omitted. Therefore, although the conjugate will reach the negative control site, it will aggregate due only to non-specific binding. Similarly, the device can include a positive control, such as with an authentic sample of the analyte for detection immobilized at the positive control site. An alternate control site can be located downstream of the capture site and have immobilized thereon at least one capture antibody (e.g., a protein). Such control site can function to capture and immobilize labeled antibody which has not been captured at the capture site. For example, such control site can include polyclonal antisera specific for the labeled antibody immobilized thereon to indicate proper functioning of the assay.

In some embodiments, a biphasic chromatographic medium (substrate/test strip) can be used in the disclosed assays and can comprise an upstream release medium joined to a downstream capture medium. The release and capture media can comprise two different materials or phases having different specific characteristics. The two phases can be joined together to form a single fluid path such that a solvent front can travel unimpeded from the proximal (upstream) end of the release medium (which can be defined as a proximal portion of the biphasic medium) to the distal (downstream) end of the capture medium (which can be defined as a distal portion of the biphasic medium). A sample receiving member can be generally provided at the proximal end of the biphasic substrate and a reservoir of sorbent material can be located beyond the biphasic substrate.

In other embodiments, a triphasic chromatographic medium (substrate/test strip) can be used in the disclosed assays and can comprise a capture medium overlapped at one end by a release medium and at the opposing end by a reservoir. The triphasic substrate can be in fluid communication with a sample receiving member at the end thereof comprising the release medium.

In certain embodiments, use of a biphasic or triphasic chromatographic medium may enhance the speed and sensitivity of an assay, such as those described in U.S. Pat. No. 6,319,676, U.S. Pat. No. 6,767,714, U.S. Pat. No. 7,045,342, and U.S. Publication No. 2012/0083044, which are incorporated herein by reference, including without limitation for the purpose of describing biphasic chromatographic media. Methods for manufacturing chromatographic media are also described in detail in U.S. Pat. No. 5,846,835, the disclosure of which is incorporated herein by reference in its entirety.

Reagents for detecting, labeling, and capturing an analyte of interest can be disposed on the release and capture media. In certain embodiments, one or more labeled conjugates can be located on the release medium and each can include a binding member (e.g., antibody) that may be reactive with a particular site (sometimes referred to as a "first epitope," "second epitope," etc.) on the analyte of interest. The labeled conjugates further can comprise one or more detectable markers (or labels), as discussed herein.

The release medium can be formed from a substance which allows for release of reagents deposited thereon, which can comprise reagents that are releasably (i.e., not permanently) bound to the release medium. The primary function of the release medium is first to support and to subsequently release and transport various immunological components of the assay, such as a labeled conjugate and/or a capturable conjugate, both of which are capable of binding to the analyte of interest. The release medium can be formed of any material capable holding, releasing, and transporting various immunological parts of the test such as the labeled test component (e.g., a bibulous, hydrophilic material).

The capture medium can be formed from a material which permits immobilization of reagents for detection of the presence of analyte in the test fluid. Immobilization can refer to any interaction that results in antibodies or analytes being irreversibly bound to the substrate such that they are not appreciably washed away, e.g., during the course of a single use of the device. The capture medium can comprise hydrophilic polymeric materials, such as microporous films or membranes, which permit protein reagents to be immobilized directly on the membrane by passive adsorption without the need for chemical or physical fixation, although fixation such is not excluded.

The release medium and capture medium can be joined via any suitable means. For example, the two media can be joined by overlapping the downstream edge of the release medium over the upstream edge of the capture medium. The various media components of the biphasic or triphasic substrate can be adhered to a clear polymer film or opaque sheet, thereby holding the media in place. Alternately, the media can be connected by a non-overlapping butt joint and may still be attached to an underlying support.

The diffusible and non-diffusible reagents can be applied to the release and capture media, respectively, by any suitable technique. In one embodiment, the diffusible antibody reagents can be applied to the release medium by direct application onto the surface of the medium and dried to form a band. Generally, reagents can be immobilized using absorption, adsorption, or ionic or covalent coupling, in accordance with any suitable methods.

Figures 1A, 1B, 1C:
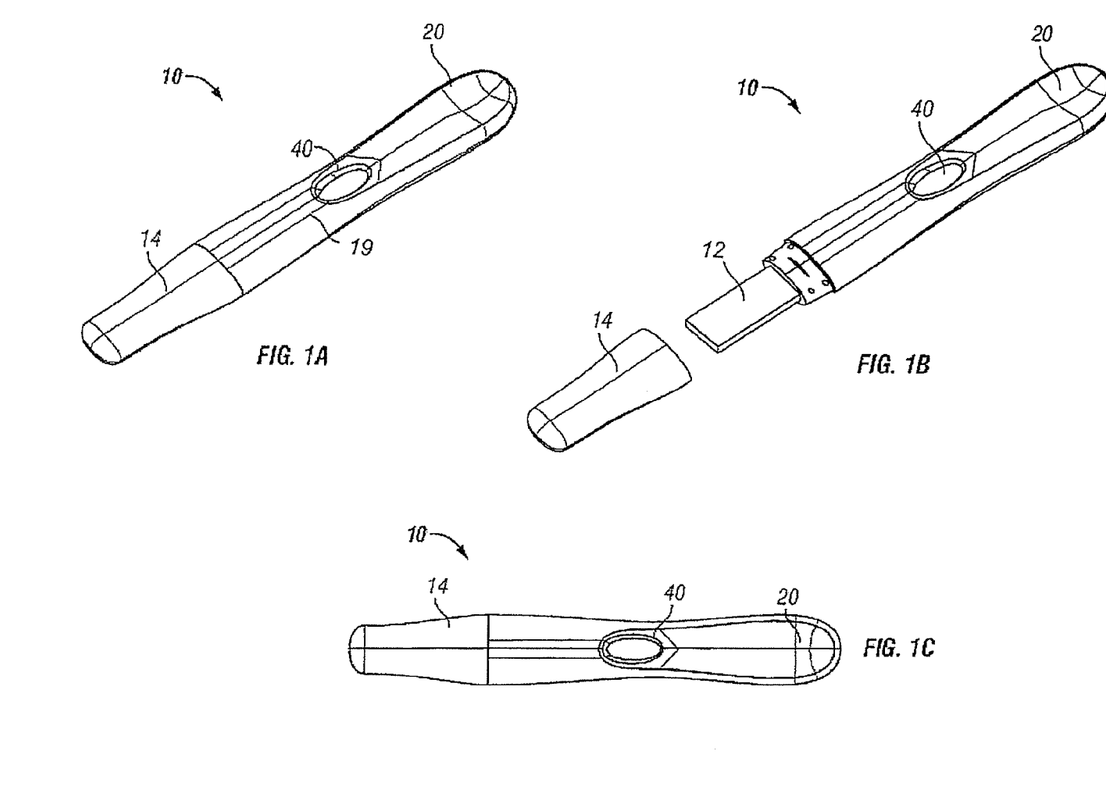
FIG. 1A shows a perspective view of an analog detection device according to one exemplary embodiment of the disclosure.
FIG. 1B shows a perspective view of the detection device of FIG. 1A with a disengaged cap.
FIG. 1C shows a top view of the detection device of FIG. 1A.

In one embodiment, a test device 10 according to the present disclosure can comprise a casing defining a sample inlet, a test volume, and reservoir volume, as illustrated in FIG. 1A-FIG. 1C. The casing 19 is generally configured to provide a recessed portion 20 shaped to permit users to place their thumb into the recessed portion and their forefinger on the bottom of the casing to securely hold the test device 10. Disposed within the casing 19 are the functional components forming a test member. The test member can be a single strip or a combination of strips of materials useful for providing an assay. For example, the test member can be a test strip as described herein, such as comprising a biphasic or triphasic substrate, for use in an assay. A sample receiving member 12 can be disposed within the casing 19, extends to the exterior thereof, and may be covered by a removable cap 14.

In use, a test sample passes from the sample receiving member 12 to a test member, such as a chromatographic substrate, where the sample is in reactive contact with the test site (e.g., the capture site), and optionally one or more control sites. A central display section 40 on the top of the casing defines a region that permits a user to observe test results as they become detectable. As described herein, "becoming detectable" specifically can relate to the accumulation of sandwich complexes at the capture site, which can be detected in various ways, such as by visual inspection of, for example, a digital readout resulting from the electronic analysis of the aggregate at the capture site as further described herein. In the embodiment illustrated, the display section 40 can provide for viewing of an analog signal, such as a colored indicator of accumulation of labeled complexes at the test site visible through the display section. Although not expressly shown, the test device 10 further can include one or more perforations in the casing to improve audibility of any audio communications that are provided from the test device, as otherwise described herein. Such perforations can be present, for example, in the location of a loudspeaker or other audio component of the test device. Further, components necessary to form an electronic communication circuit can be retained with the casing of the test device, as otherwise described herein. More particularly, one or a series of holes, slots, or the like can be present to improve sound transmission from the device.

Figure 2A:
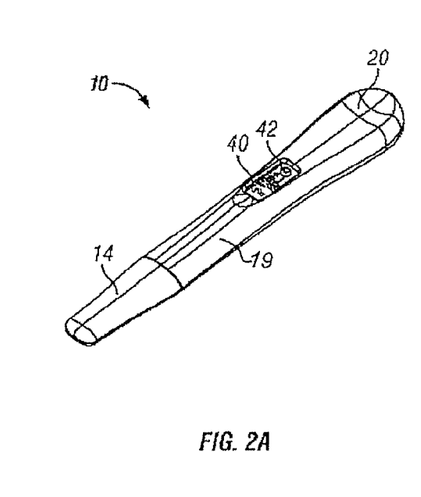
FIG. 2A shows a perspective view of a digital detection device according to one exemplary embodiment of the disclosure.
Figure 2B:
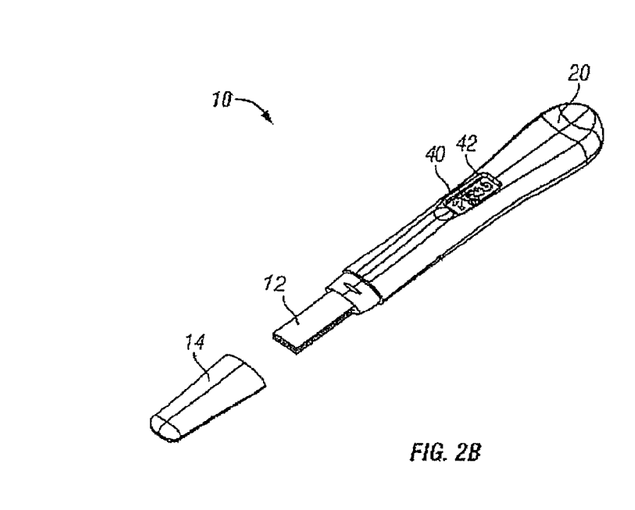
FIG. 2B shows a perspective view of the detection device of FIG. 2A with a disengaged cap.
Figure 2C:
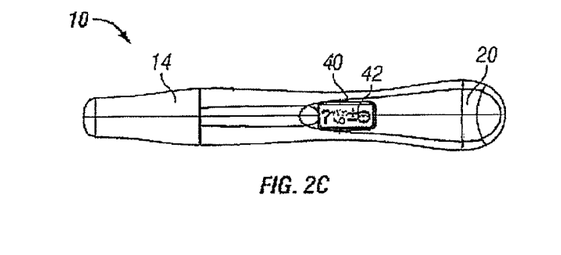
FIG. 2C shows a top view of the detection device of FIG. 2A.

A further embodiment is illustrated in FIG. 2A-FIG. 2C. Again, the test device 10 is formed of a casing 19 that comprises a recessed portion 20 at a back portion thereof and that comprises a sample receiving member 12 at a front portion thereof that extends into the casing. The sample receiving member 12 preferably is covered by a removable cap 14. In this embodiment, the central display section 40 includes an underlying display screen 42 that can provide digital displays of one or more statuses and results of the test device. The casing 19 can enclose a suitable test member (e.g., a biphasic or triphasic substrate and associated elements, such as a reservoir).

In the use of one exemplary assay, a sample passes through the inlet defined by the sample receiving member and into the interior of a device, where it comes into contact with the test member including a release medium and a capture medium. If the analyte of interest is present in the sample, it binds to the one or more labeled antibodies which are releasably attached to the release medium. The sample, now comprising analyte-labeled antibody conjugates, wicks up the release medium and forms a sandwich complex with one or more capture antibodies immobilized on the capture medium (defining a capture site or test site). As the sample front passes across the capture site, a complex is formed comprising the analyte, labeled antibody, and the capture antibody. This "sandwich" complex can be analyzed by detecting the presence of the label at the capture site. Detection can be via a visual review of a colored color in the display section of an analog device or via viewing a digital readout on, for example, an LCD screen of a digital device. As further discussed herein, detection also can include audible signals or words. Although the present disclosure is described largely in terms of direct devices/direct detection, other devices (i.e., affinity-based devices) are also intended to be encompassed herein. Affinity-based devices operate on similar principles, but rely on indirect binding (wherein one member of an affinity pair (e.g., biotin) is present on a capturable conjugate (and subsequently on any diffusible sandwich complex formed therefrom) and the other member of the affinity pair (e.g., avidin) is present on the capture medium section of the substrate).

Figure 3A:
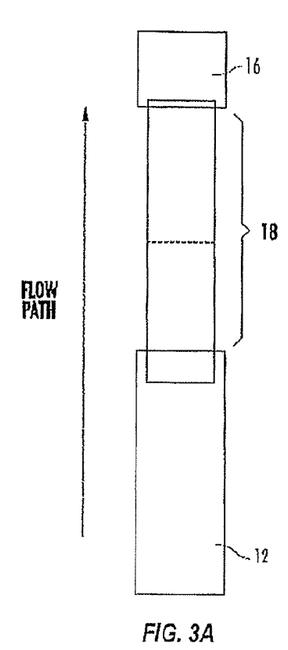
FIG. 3A shows a top view of lateral flow test components according to one exemplary embodiment of the disclosure comprising a reservoir absorbent material, a biphasic substrate, and a sample receiving member outside of a casing.

FIG. 3A shows an example of lateral flow test components that can be present in a device such as illustrated in FIG. 1A-FIG. 1C. These test components can comprise a sample receiving member 12, biphasic chromatographic substrate 18, and reservoir absorbent material 16. When the device is placed in contact with a fluid sample, the fluid is transported by capillary action, wicking, or simple wetting along the flow path downstream through sample receiving member 12, along chromatographic substrate 18, and into reservoir absorbent material 16, generally as depicted by the arrow. Sample receiving member 12 may also serve as a filter which can remove particulate matter and interfering factors from a sample. The sample receiving member 12 preferably is a bibulous hydrophilic material which facilitates absorption and transport of a fluid sample to the biphasic chromatographic substrate 18. Such materials may include cellulose acetate, hydrophilic polyester, or other materials having similar properties. A combination of absorbent materials also may be used. As noted above, a filtration means which limits the introduction to the test site of contaminants from the sample may also be included. In certain embodiments, the sample receiving member 12 can be omitted, and the release medium of a biphasic substrate 18 can itself act as the sample receiving member. Such embodiments of the assay materials are useful in performing dipstick assays. By providing a reservoir of sorbent material (e.g., absorbent paper made from cotton long linter fibers or cellulosic materials) disposed beyond the chromatographic substrate, a relatively large volume of the test fluid and any analyte it contains can be drawn through the test area to facilitate background clearance and thereby aid sensitivity. The reservoir absorbent generally facilitates capillary action along the chromatographic substrate and absorbs excess fluid contained within the device.

Figure 3B:
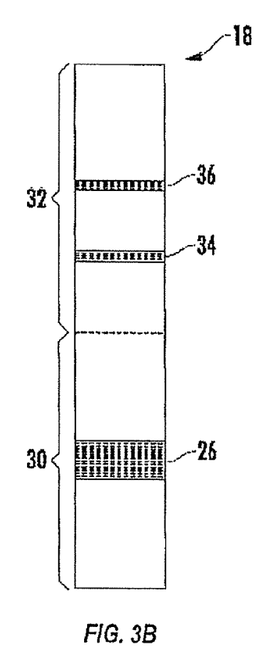
FIG. 3B shows a top view of a biphasic substrate for use in a test device according to an exemplary embodiment of the disclosure.

FIG. 3B illustrates in greater detail an exemplary biphasic chromatographic substrate 18, comprising a release medium 30 and a capture medium 32 joined together to form a single fluid path. A band 26 of labeled binding member, e.g., an antibody-metal sol, can be releasably disposed on the release medium 30. In one embodiment, the labeled binding member is in dehydrated form. As the fluid sample moves past the band 26, the labeled binding member becomes entrained in the fluid, reconstituted (in the case of a dehydrated binding member), and binds with a particular analyte or analytes of interest present in the fluid sample. Accordingly, the resulting complex comprising a binding antibody, a label component, and an analyte for identification (e.g., hCG) advances along with the sample front until it reaches the capture site 34. In this particular embodiment, the capture site includes at least one immobilized capture antibody which binds to a different epitope of the analyte. Accordingly, a sandwich complex including the desired analyte is formed at the capture site 34. If desired, a control site 36 can be present.

Figure 4A:
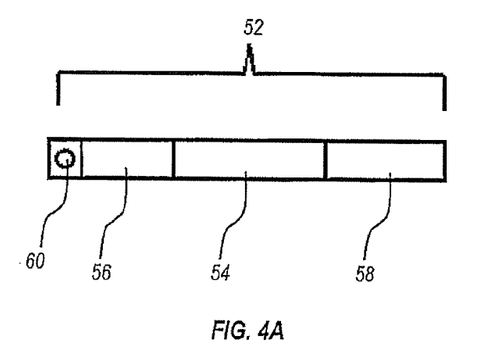
FIG. 4A shows a top view of a lateral flow test strip comprising a triphasic substrate according to an exemplary embodiment of the disclosure.
Figure 4B:
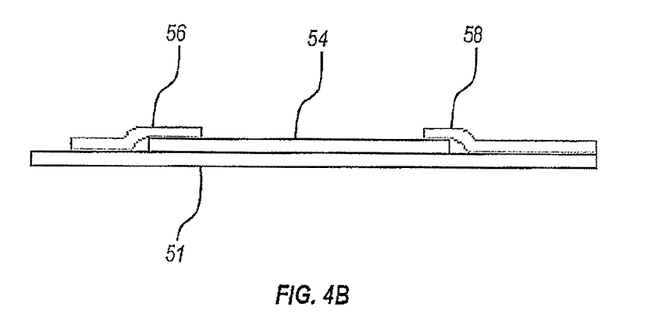
FIG. 4B shows a side view of the triphasic substrate of FIG. 4A.

A further exemplary lateral flow test strip that can be present in a device according to the present disclosure is illustrated in FIG. 4A. In particular, a triphasic test strip 52 is shown and is formed of a release medium 58, a capture medium 54, and a reservoir 56. An alignment hole 60 is shown and can be used to align the test strip within a casing by mating with an appropriately positioned pin. FIG. 4B illustrates an overlapping relation of the release medium 58, capture medium 54, and reservoir 56. Although not illustrated, the release medium 58 can be in fluid communication with a sample receiving member as already described herein. Further, the release medium 58, capture medium 54, and reservoir 56 can be laminated onto a backing 51, which can be, for example, an opaque plastic film or sheet. In use, the appropriate antibodies, binding members, and labels can be positioned on the release medium 58 and the capture medium 54, and an advancing fluid sample can cause formation of a complex, such as, for example, the combination of a binding antibody, a label component, and an analyte for identification. This complex then can bind with a binding member on the capture medium 54. The resulting, bound complex can be analyzed by the detection means as otherwise discussed herein, and a result then can be provided via an LCD screen, for example, visible through the central display section 40. The release and capture media can be constructed of materials as described above in relation to a biphasic substrate embodiment.

For further detail regarding various testing devices, methods of use, and parameters thereof, see for example U.S. Pat. Nos. 5,739,041; 6,046,057; 6,277,650; 6,319,676; 6,767,714; 7,045,342, 7,763,454; 7,776,618 and 8,211,711 to Nazareth et al., and U.S. Patent Application Publication Nos. 2002/0042082, 2004/0171174; 2008/0213920; 2010/0051350; 2010/0239460; 2010/0240149; 2010/0261293; 2010/0267166; and 2011/0201122 to Nazareth et al., and 2012/0083044 to Sturman et al.; which are incorporated herein by reference in their entireties.

Communication components of the test devices disclosed herein beneficially can provide for improvements not only in communicating test results but also in providing additional information to a user that can impart an improved sense of connectivity of the user with the device. A variety of indices of operation can be communicated to a user during and/or after use of the present devices. In certain embodiments an indication of the functioning of the device and/or the results of the test being carried out can be identified to the user by providing one or more digital outputs, including but not limited to words, symbols, sounds, and colors that may be read or otherwise interpreted by the user. Such embodiments can comprise, for example, an opto-electronic reader coupled with a software program which can evaluate various parameters (e.g., chemical parameters or physical parameters) at the capture site. The program software can provide additional functions, as otherwise described herein. A variety of analog and/or digital outputs thus can be encompassed by the devices disclosed herein, and such outputs can communicate multiple different types of information to a user of the device.

In specific embodiments, a test device according to the present disclosure can comprise assay components, such as those described herein, that are effective to carry out a diagnostic test on a fluid sample and identify (qualitatively as well as quantitatively) the presence of an analyte in the sample. The test device also can comprise at least one electronic control component (e.g., a microcontroller) and at least one audio component. Further, the test device can comprise one or more components adapted to provide input signals to the microcontroller relating to the assay. Moreover, the microcontroller can include programming such that the microcontroller is adapted to respond to a defined input signal by signaling the audio component to output or emit a corresponding audio signal. These elements of a test device according to various embodiments of the present disclosure are discussed in greater detail below.

Figure 5:
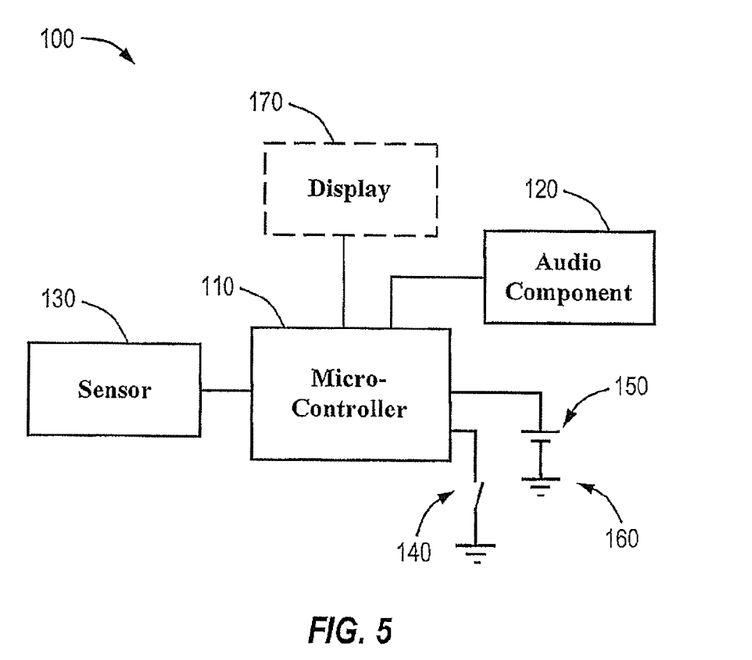
FIG. 5 is a schematic of operational components of an electronic communication circuit of a test device arranged to provide audible external communication, according to one exemplary embodiment of the disclosure.

In relation to certain embodiments, a schematic of operational components of an electronic communication circuit 100 useful according to the present disclosure is shown in FIG. 5. The communication circuit utilized in the test device generally can include all components necessary to generate an input signal, process the input signal, direct a defined output signal in response to the input signal, and execute the output signal so as to deliver an audible indicia of an operation of the test device. The communication circuit can include a microcontroller 110 that is adapted to direct the overall functions of the test device, process information about the assay (such as described above), and output signals to cause formation of audible tones or messages that can be understood or interpreted by a user. If desired, a microprocessor may be utilized so long as any further hardware or software necessary to carry out the functions of the test device are included as well (e.g., RAM or ROM). Controllers and processors that are commercially available can be adapted for use according to the present disclosure. Preferably, the controller includes programming (e.g., embedded software) that includes the requisite definitions of input signals and associated output signals to enable to the controller to direct the communication functions of the test device, as otherwise disclosed herein.

The communication circuit 100 further can include a sensor 130 that is adapted to detect a condition, signal, state, or result of the associated test and thus form an input signal. The sensor or detector is electrically connected to the microcontroller 110 such that the microcontroller can process the input signal from the sensor and act accordingly thereon. A variety of sensors can be used according to the present disclosure. For example, opto-electronic detectors and similar combinations of light sources (e.g., LEDs) and light sensors can be used to electronically read a signal formed at a test site, such as through agglomeration of labeled antibodies, as discussed above. Such sensors can provide a qualitative input signal (i.e., a yes/no or 1/0 based upon whether a detectable signal is or is not formed at the test site) and can also provide a quantitative input signal (i.e., estimating an analyte concentration based upon a programmed reference value, such as can be estimated based upon color or color intensity at a test site). Such detectors also can be utilized to identify application of a fluid sample to a portion of the assay, such as a sample receiving member 12 (referencing FIG. 2B), a release medium 58 (referencing FIG. 4B), or a capture medium 54 (referencing FIG. 4B). In other embodiments, moisture sensors can be used to detect the application of the fluid sample, and such sensors can be calibrated to provide the input signal only when a defined moisture level is attained so as to be indicative of the application of a sufficient volume of fluid for the assay to proceed according to normal operation. The moisture sensor can be located in fluid communication with one or more of the sample receiving member, the release medium, and the capture medium in order to determine if sufficient sample has been applied to drive the assay to completion.

The communication circuit 100 further includes an audio component 120 that is electrically connected to the microcontroller 110 such that the microcontroller can deliver output signals to the audio component for execution. The nature of the audio component can in part be based upon the nature of the audio communication to be delivered by the test device. For example, in certain embodiments, the audio component can be configured to deliver and output sound that can be selected from the group consisting of a single tone, a series of tones, a melody, a synthesized word or words, a recorded word or words, and combinations thereof. Audio elements necessary to achieve one or more of these outputs can be included in the test device.

In some embodiments, the audio component can comprise a transducer. For example, a surface-mount audio transducer can be provided on an integrated circuit (including the same IC as the microcontroller, if desired), and the selection thereof can vary based upon the desired sound pitch, response time, voltage, sound that is output, and size. In some embodiments, an audio driver can be self-contained within a transducer. In other embodiments, an appropriate audio driver can be utilized in addition to the transducer or buzzer. The use of such devices as the audio component can be particularly beneficial in embodiments where only relatively simple audio outputs are desired, such as a single tone or beep or a series of tones or beeps. For example, the microcontroller can generate an output signal that is a fixed frequency signal that is passed through an audio driver that drives a loudspeaker or buzzer. Alternatively, the microcontroller can provide a logic level signal to turn on a self-contained audio driver with built-in oscillator that generates a beep or other tone or tones when directed by the logic signal. The microcontroller thus can determine when to generate the appropriate output signal depending upon the state of the assay.

As a non-limiting example, the communication circuit 100 can include an assay initiation routine (e.g., as part of the embedded software in the microcontroller 110) that can be triggered by an on switch 160. For example, the removal of the cap 14 from the test device 10 can automatically trigger power to flow from the power source 150 (e.g., a battery) to further components of the communication circuit. Such trigger may be via mechanical or optical (i.e., a light sensor) means, and the switch 160 can vary accordingly and can be independent of the cap. This can function as an input signal to the microcontroller to generate an output signal to the audio component to output one beep or a series of beeps as indication that the test is activated. Similarly, when a moisture sensor indicates that a sufficient volume of fluid sample has been deposited on the test strip, the microcontroller can generate an output signal to the audio component to output one beep or a series of beeps as indication that the requisite fluid sample has been applied. Likewise, simple beeps can be generated periodically while the assay is being carried out and/or when the assay is complete and a test result is available. If desired, the length of a beep tone or the time gap between beeps can be varied. Beeps of different tone or a series of beeps or tones can be used to indicate that different stages of the assay are underway or to communicate different assay results—e.g., two audibly different beep tone frequencies, two intermittent beep tones of audibly different types, or two beep tones of different lengths are non-limiting examples. For example, while the assay is processing, periodic beeps can be directed as indication of the processing, and the period of the beeps can become shorter as the assay nears completion.

If desired, a display can be present on the test device. For example, the central display section 40 can provide an analog or digital display of the assay results. Specifically, the display can reveal a visual signal of the accumulation of labeled antibodies at the test site. Alternatively, an LCD display can be provided to digitally provide a visual signal. Words or symbols can be shown on the display, and such visual indicators can correlate to one or more of the audible signals provided by the test device. For example, a specific audible signal can indicate that the assay is completed and the test results are available for viewing in the display. As illustrated in FIG. 5, the display 170 can be an optional element of the communication circuit 100. As such, the audible signals can be entirely utilized to provide all indicia related to the test device, including relaying the results of the assay.

If desired, the communication circuit can include an audio switch 140 adapted to enable or disable the audio output. For example, the switch can provide a logic 0 or 1 input to the microcontroller 110 to either allow or disallow signal delivery from the microcontroller to the audio component 120. Likewise, a volume control component can be present.

Figure 6:
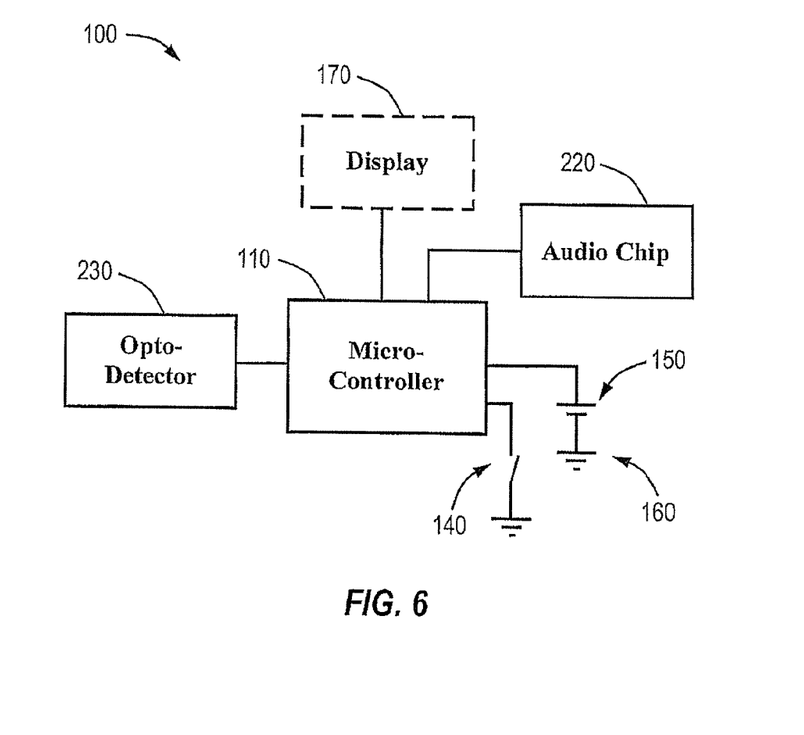
FIG. 6 is a schematic of operational components of an electronic communication circuit of a test device arranged to provide audible external communication, according to another exemplary embodiment of the disclosure.

In further embodiments, the richness of the audio features of the test device can be increased with the choice of further audio components. FIG. 6 illustrates an exemplary embodiment of a communication circuit 100 of the present disclosure with increased functionality. As seen therein, the communication circuit utilizes an audio chip 220 as the audio component. The audio chip preferably includes or is in electrical connection with a loudspeaker or buzzer. Moreover, the audio chip preferably includes a memory driver, and the chip can have integrated RAM or ROM including programming for a variety of sounds to be produced by the test device. Alternatively, the RAM or ROM of the microcontroller 110 can include the necessary programming to direct the appropriate audio output. According to such embodiments, the audio chip can function to synthesize an audio waveform from a set or sets of digital values stored in a memory component of the communication circuit 100, such as described above. The microcontroller can provide the output signals to the audio chip that direct the audio chip to create one or more audio sequences to be output from the chip, such as through the loudspeaker or broadband buzzer element. As before, the audio output can include simple tones; however, in the present embodiment, more complex musical sequences and synthesized words or recorded human speech can be output based on the stored sequences of digital states in the memory.

The inclusion of the audio chip 220 provides for a wide array of audible output from the communication circuit 100. For example, the assay initiation routine (e.g., triggered by removal of the cap 14) can signal the microcontroller to provide an output to the audio chip to make an audio output in the form of synthesized or recorded language that provides one or more instructions to the user in relation to steps necessary to carry out the assay with the test device. Language relaying other types of information to the user also can be provided. Once the assay has been initiated by the user (i.e., through application of fluid sample), the microcontroller can instruct the audio chip to indicate audibly that the test has been started. In particular, the communication circuit 100 can include an opto-detector 230 comprised of a light source, such as one or more LEDs and one or more light sensors that can be calibrated to detect indicia of operation of the assay at the sample receiving member 12, the release medium 58, or the capture medium 54. Alternatively (or in addition), the communication circuit also can include a moisture sensor. Audible indication of the assay start can be as described above and can include spoken indication. The audio chip also can be adapted to output information in relation to the test time elapsed and/or remaining for the assay to reach completion (generally less than about 5 minutes from the time of fluid sample application). For example, tones as discussed above can be provided. In further embodiments, a musical tune can be played for all or part of the assay processing time. Alternatively, spoken messages can be provided during the processing time to provide reassurance to the user of proper function. Moreover, spoken messages can include further instructions related to the assay, marketing messages, or the like. When the assay has reached completion, the audio chip can receive and execute instructions for output indicating that the test time has elapsed and can also provide audio indication of the assay results and/or direct the user to reference the optional display to view the test results. Again, spoken words (synthesized or recorded) can be used in relation to this function.

Figure 7:
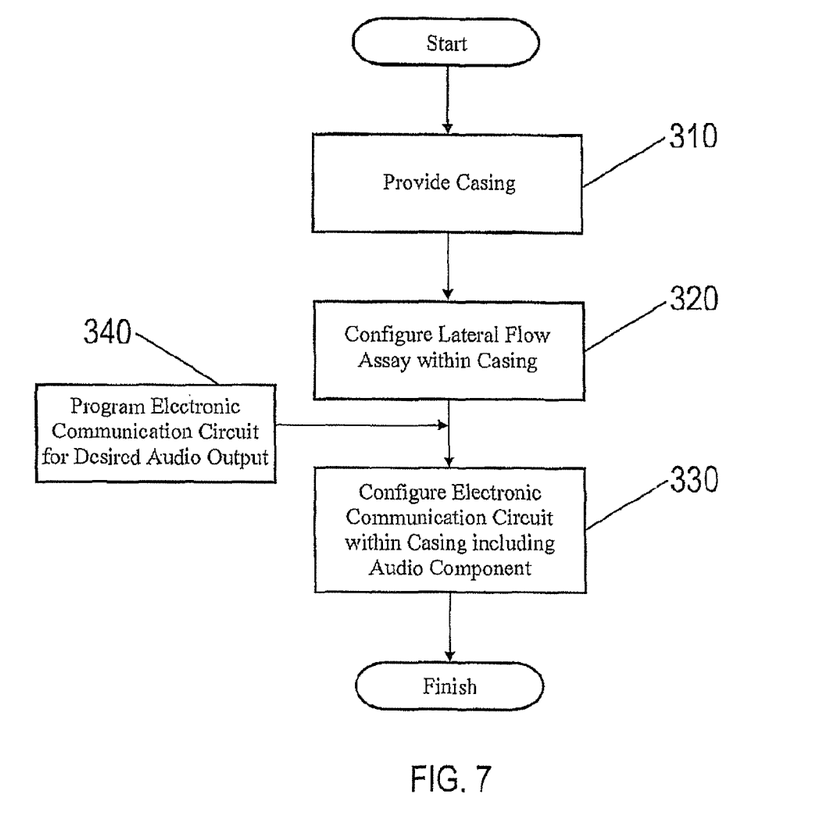
FIG. 7 is a flow chart illustrating an exemplary embodiment of a method for providing one or more indicia of operation of a lateral flow assay to a user through formation of an appropriate test device.

The present disclosure also provides for methods for providing one or more indicia of operation of a lateral flow assay to a user. In particular, the methods can include steps for the manufacture of a test device, such as otherwise described herein. An exemplary embodiment of the methods of the disclosure is shown in FIG. 7. For example, a test device casing can be provided 310. The components of a lateral flow assay can be incorporated into the casing 320.

Moreover, elements forming an electronic communication circuit also can be incorporated into the casing 330. Specifically, a microcontroller element can be provided along with one or more components adapted to provide input signals to the microcontroller relating to the lateral flow assay. Further, one or more audio output elements can be included in the casing. In specific embodiments, the methods can comprise programming the microcontroller to respond to a defined input signal by signaling the audio output component to emit a corresponding audio signal 340. Such step can be carried out through application of the appropriate hardware and/or software that is adapted to create stored commands and execution routines within the communication circuit. The method further can comprise selection of appropriate audio components to output the desired type of audio—e.g., a single tone, a series of tones, a melody, a synthesized word or words, a recorded word or words, and combinations thereof.

Many modifications and other embodiments of the disclosure set forth herein will come to mind to one skilled in the art to which these disclosure pertain having the benefit of the teachings presented in the foregoing descriptions. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A diagnostic test device comprising: a test member; and an electronic communication circuit providing one or more indicia of operation of the test member to a user; wherein the electronic communication circuit includes an audio output component comprising an audio chip that includes a memory driver having digital values stored therein, and includes a microcontroller signaling the audio output component to provide an audible indicia of operation of the test member; and wherein the signal from the microcontroller is configured to instruct the audio chip to create the audible indicia of operation from the stored digital values in the memory driver of the audio chip.

2. The diagnostic test device of claim 1, wherein the audio output component further comprises a transducer.

3. The diagnostic test device of claim 1, wherein the audio output component comprises an audio driver.

4. The diagnostic test device of claim 1, further comprising a switching element enabling or disabling the audio output component.

5. The diagnostic test device of claim 1, wherein the electronic communication circuit further comprises one or more components providing input signals relating to the test to the microcontroller.

6. The diagnostic test device of claim 5, wherein the one or more components providing input signals is one or more of the following: a light source; a light sensor; a moisture sensor.

7. The diagnostic test device of claim 1, wherein the electronic communication circuit further includes a display.

8. The diagnostic test device of claim 1, wherein the electronic communication circuit further comprises a power source.

9. The diagnostic test device of claim 1, wherein the test device detects the presence of an analyte in a fluid sample applied to the test member.

10. The diagnostic test device of claim 9, wherein the analyte is selected from the group consisting of human chorionic gonadotropin (hCG), luteinizing hormone (LH), follicle stimulating hormone (FSH), thyroid stimulating hormone, estrogen, progesterone, testosterone, a metabolite thereof, and combinations thereof.

11. The diagnostic test device of claim 1, further comprising a sample receiving member in fluid communication with the test member.

12. The diagnostic test device of claim 1, wherein the microcontroller signals the audio output component to indicate one or more of the following:
a sufficient volume of fluid sample has been deposited on a sample receiving member of the test device for the test to be carried out;
the test device is processing an applied fluid sample;
the test device has completed processing an applied fluid sample;
a test result arising from the test device having processed an applied fluid sample.

13. The diagnostic test device of claim 1, wherein the test device further comprises components suitable to carry out a test initiation routine.

14. The diagnostic test device of claim 13, wherein the components include a signaling mechanism in communication with the microcontroller.

15. The diagnostic test device of claim 1, wherein the test member comprises a release medium in fluid communication with a capture medium.

16. The diagnostic test device of claim 1, further comprising a sample receiving member in fluid communication with the test member.

17. A method providing one or more indicia of operation of a test device to a user, the method comprising combining, in a single casing:
a test member; and
an electronic communication circuit that includes:
an audio output component comprising an audio chip that includes a memory driver having digital values stored therein;
a microcontroller signaling the audio output component to provide an audible indicia of operation of the test member, wherein the signal from the microcontroller is configured to instruct the audio chip to create the audible indicia of operation from the stored digital values in the memory driver of the audio chip; and
one or more components providing input signals to the microcontroller relating to the test member.

18. The method of claim 17, further comprising programming the microcontroller to respond to a defined input signal by signaling the audio output component to emit a corresponding audio signal.

19. The method of claim 18, wherein audio signal is selected from the group consisting of buzzing, a single tone, a series of tones, a melody, a synthesized word or words, a recorded word or words, and combinations thereof.

* * * * *